United States Patent [19]

Mixan et al.

[11] 4,052,394

[45] Oct. 4, 1977

[54] 2-(DICYANOMETHYLENE)-1,3-DITHIOLO-(4,5-b)PYRAZINE-5,6-DICARBONITRILE

[75] Inventors: Craig E. Mixan; R. Garth Pews, both of Midland, Mich.

[73] Assignee: The Dow Chemical Company, Midland, Mich.

[21] Appl. No.: 744,485

[22] Filed: Nov. 24, 1976

[51] Int. Cl.² .......................................... C07D 495/04
[52] U.S. Cl. ............................ 260/250 BC; 424/250
[58] Field of Search .................................. 260/250 BC

[56] References Cited

U.S. PATENT DOCUMENTS

| 3,761,475 | 9/1973 | Kurihara et al. | 260/250 R |
| 3,879,394 | 4/1975 | Donald | 260/250 BN |

OTHER PUBLICATIONS

William O. Foye et al., J. Pharmaceutical Sciences, vol. 57, No. 9, pp. 1611–1613, (1968).

Primary Examiner—Donald G. Daus
Assistant Examiner—Jose Tovar
Attorney, Agent, or Firm—Theodore Post; C. Kenneth Bjork

[57] ABSTRACT

2-(Dicyanomethylene)-1,3-dithiolo(4,5-b)pyrazine-5,6-dicarbonitrile is prepared by reacting di(sodiomercapto)methylenemalononitrile with 2,3-dichloro-5,6-dicyanopyrazine in dimethylformamide as reaction medium at a temperature between about 25° and about 60° C until reaction is substantially complete. The reaction product has antimicrobial utility.

1 Claim, No Drawings

2-(DICYANOMETHYLENE)-1,3-DITHIOLO-(4,5-b)PYRAZINE-5,6-DICARBONITRILE

DESCRIPTION OF PRIOR ART FOUND

N. H. Kurihara, U.S. Pat No. 3,761,475, patented Sept. 25, 1973, discloses certain polycyanodithiino aromatic N-heterocyclic compounds which are said to be useful as fungicides and bactericides. Among the compounds therein disclosed is the 2,3-dicyano[p-dithiino(2,3-b)pyrazine-6,7-diyl]. W. O. Foye e.a., J. Pharm. Sci., 57 1611 (1968) disclose 2-dicyanomethylenepyrazino[2,3-d]dithiole.

SUMMARY OF THE INVENTION 2-(dicyanomethylene)-1,3-dithiolo(4,5-b)pyrazine-5,6-dicarbonitrile is prepared by adding 2,3-dichloro-5,6-dicyanopyrazine dissolved in dimethylformamide to a substantially equimolar proportion of a solution of di(sodiomercapto)methylenemalononitrile in dimethylformamide. The reaction mixture is stirred at about 25° to about 60° C until substantial completion of the reaction, usually from about 8 to about 72 hours. Upon completion of the reaction, the mixture is poured into ice water and the crude solid product which precipitates is recovered by filtration. The product is purified by dissolving in a mixture of acetone and chloroform, decolorizing the solution with charcoal, drying over desiccant-grade magnesium sulfate and recrystallizing the dried product from chloroform. The product melts at about 280° C with decomposition.

DESCRIPTION OF A PREFERRED EMBODIMENT

The following additional description and example further describe the invention and the manner and process of making and using it to enable the art skilled to make and use the same and set froth the best mode contemplated by the inventors of carrying out the invention.

In the conventional in vitro agar Petri dish dilution tests for determining bactericidal and fungicidal activity, the compound of this invention gave 100% inhibition in growth of the following microorganisms at the indicated concentrations in parts per million:

| IN VITRO MINIMUM INHIBITORY CONCENTRATION, PPM | | | | | | | | | | | | | | |
|---|---|---|---|---|---|---|---|---|---|---|---|---|---|---|
| Compound | Sa* | St | Aa | Pa | Bs | Kp | Sm | Ca | Cp | Tg | Ap | Ci | Tm | Pc | Af | An |
| [structure] | 5 | 10 | 100 | 500 | 5 | 100 | 50 | 5 | 5 | 10 | 10 | 5 | 5 | 5 | 5 | 5 |

*S. aureus  
B. subtilis  
C. pelliculosa  
T. mentagrophytes  
S. typhosa  
K. pneumoniae  
T. globrata  
P. chrysogenum  
A. aerogenes  
S. marcescens  
A. pullulans  
A. fumigatus  
P. aeruginosa  
C. albicans  
C. ips  
A. niger

EXAMPLE

2-(Dicyanomethylene)-1,3-dithiolo-(4,5-b)-pyrazine-5,6-dicarbonitrile

To a stirred solution of 9.3 g (0.05 mol) of disodium dimercaptomethylenemalononitrile in 100 ml of dimethylformamide was gradually added 10 g (0.05 mol) of 2,3-dichloro-5,6-dicyanopyrazine in 70 ml of dimethylformamide. The reaction mixture was stirred at 40° C for 8 hours and poured into 700 ml of water. The resulting solid was collected by suction filtration, washed with water, and dried. The crude product was dissolved in acetone-$CHCl_3$, decolorized with charcoal and dried over $MgSO_4$. Recrystallization from $CHCl_3$ yields 5.0 g (37%) of yellow crystals. M.p. ~280° C (dec.). $\nu$CN ($cm^{-1}$): 2220.

Anal. Calcd for $C_{10}N_6S_2$: C, 44.78; N, 31.34; S, 23.88. Found: C, 44.6; N, 31.13; S, 23.6.

PREPARATION OF STARTING MATERIALS

Di(sodiomercapto)methylenemalononitrile is preparted by the method of A. Adams et al., J. Chem. Soc. 3061 (1959). 2,3-Dichloro-5,6-dicyanopyrazine is prepared by the method of D. S. Donald, U.S. Pat. No. 3,879,394, patented Apr. 22, 1975.

What is claimed is:
1. 2-(Dicyanomethylene)-1,3-dithiolo(4,5-b)-pyrazine-5,6-dicarbonitrile.